United States Patent [19]

Graham et al.

[11] Patent Number: 4,886,754

[45] Date of Patent: Dec. 12, 1989

[54] RECOMBINANT BATERIOPHAGE FOR HETEROLOGOUS CLONING OF BACILLUS MICROORGANISMS AND METHOD FOR ITS PRODUCTION

[75] Inventors: Richard S. Graham; Yuko Yoneda; Frank E. Young, all of Rochester, N.Y.

[73] Assignee: The University of Rochester, Rochester, N.Y.

[21] Appl. No.: 740,312

[22] Filed: Jun. 3, 1985

Related U.S. Application Data

[63] Continuation of Ser. No. 350,923, Feb. 22, 1982, abandoned, which is a continuation of Ser. No. 110,042, Jan. 7, 1980, abandoned.

[51] Int. Cl.[4] .................... C12N 15/00; C12N 9/28; C12N 7/00; C12N 1/20; C12P 21/00; C12R 1/07; C12R 1/125
[52] U.S. Cl. .................... 435/172.3; 435/69.1; 435/172.1; 435/202; 435/235; 435/832; 435/839; 435/252.31; 935/31; 935/58; 935/74
[58] Field of Search .................... 435/68, 70, 71, 91, 435/172.3, 201, 202, 235, 253, 317, 832, 836, 839, 172.1, 320, 252.3, 252.31-252.35; 935/31, 57, 58, 74

[56] References Cited

U.S. PATENT DOCUMENTS 4,190,495 2/1980 Curtiss .............................. 435/172.3
4,237,224 12/1980 Cohen et al. .......................... 435/68

FOREIGN PATENT DOCUMENTS 0057976 8/1982 European Pat. Off. ............. 435/202
7776480 6/1977 Japan ................................... 435/172

OTHER PUBLICATIONS

The Microbial World, 1976, Stainer et al., ed.), Prentice-Hall, Inc., Englewood Cliffs, N.J., p. 645.
Kawamura et al: Gene 5, 87 (1979).
Yoneda et al., "Transformation of *Bacillus Subtilis* in α-Amylase Productivity, by Deoxy Ribonucleic Acid from *B. Subtilis Var. Amylosacchariticus*", J. Bact., vol. 120, No. 3 (1974), pp. 1144-1150.
Matsumoto et al., "Genetic Detects in DNA Repair System and Enhancement of Intergenote Transformation", Efficiency in Bacillus, Abst. No. 1259695, Subtilis Marburg, Chem. Absts., vol. 89, No. 15, p. 300 (1978).
"Screening of High Yield α-Amylase-Producing Strains, Shanghai Inst. Biochem., from *Bacillus Subtilis 168, by Transformation*", Chem. Absts., vol. 91, No. 1, p. 242 (1979), Absts. No. 2363.
Yasbin et al., "The Influence of Temperature Bacteriophage, 0105 on Transformation and Transfection in *Bacillus Subtilis*", Biochem. Biophys. Res. Comm., vol. 47, No. 2 (1972), pp. 365-371.
Yoneda et al., "Cloning of a Foreign Gene Cooling for α-Amylase in *Bacillus Subtilis*, Biochem. Biophys Res. Comm.", vol. 91, No. 4 (1979), pp. 1556-1564.
Wilson et al., "Intergenetic Transformation of the *Bacillus Subtilis Genospecies*", J. Bact., vol. 111 (1972), pp. 705-716.
Yasbin et al., "Transformation and Transfection in Lysogenic Strains of *Bacillus Subtilis: Evidence for Selective Induction of Prophage in Competion Cells*", J. Bact., vol. 121, No. 1 (1975), pp. 296-304.
Yasbin et al., "Effect of Lysogany on Transfection and Transfection Enhancement in *Bacillus Subtilis*", J. Bact., vol. 121, No. 1 (1975), pp. 305-312.

*Primary Examiner*—James Martinell
*Attorney, Agent, or Firm*—Martin Lukacher

[57] ABSTRACT

A recombinant bacteriophage, a method for producing and selecting the recombinant bacteriophage and a method for heterologous cloning of DNA are disclosed. The recombinant bacteriophage is produced by ligating genetic fragments encoding a desired genetic trait with DNA from a bacteriophage, incubating with DNA from a second Bacillus microorganism prototrophic for a growth requirement, incubating with a host Bacillus auxotrophic for the growth requirement. Transformed host Bacillus are selected by growing the mixture on a growth medium which does not contain the growth requirement and determining the presence of the genetic trait. The recombinant bacteriophage containing the desired genetic trait is recovered from the host Bacillus by induction. Heterologous cloning can be accomplished by incubating a host Bacillus with the recombinant bacteriophage.

2 Claims, No Drawings

RECOMBINANT BATERIOPHAGE FOR HETEROLOGOUS CLONING OF BACILLUS MICROORGANISMS AND METHOD FOR ITS PRODUCTION

This is a continuation of application Ser. No. 350,923 filed Feb. 22, 1982, now abandoned, which is a continuation of application Ser. No. 110,042 filed Jan. 7, 1980, now abandoned.

BACKGROUND AND PRIOR ART OF THE INVENTION

It is well known that the genetic information of all cells is stored in deoxyribonucleic acid (DNA) in the chromosomal material of organisms. The unit of genetic function, i.e., the locus on the chromosome related to a specific hereditary trait, is called a gene.

Recombinant DNA technology involves the transfer of genetic material (genes, or DNA fragments) from one organism into a second organism, by means of a transfer component designated a "vector", producing a combination of genetic material. The second organism (which contains the transferred genetic material) is designated a recombinant component. The recombinant component is then inserted into bacterial and animal cells for propagation of the combined genes contained in the recombinant component. The cell into which the recombinant component is inserted is designated a host cell.

One type of vector comprises bacteriophages, which are viruses that infect bacteria. A typical bacteriophage consists of nucleic acid enclosed in a protein coat.

Using recombinant DNA technology, genetic modification can be accomplished as follows. Specific DNA fragments from bacteriophages and DNA from a bacteria are "isolated", e.g., by treatment with appropriate restriction enzymes which act as "chemical scalpels" to split DNA molecules into specific fragments which usually contain from less than 1 to 10 genes each, or by other well known techniques. A DNA fragment for the desired genetic characteristic, i.e., "foreign DNA" from the bacteria source is then inserted into the DNA bacteriophage vector. By treatment with DNA ligase the DNA fragment is inserted into the bacteriophage DNA vector and a recombinant bacteriophage DNA molecule is formed. The recombinant bacteriophage contains the genes of the bacteriophage plus the new genes (foreign DNA) from the inserted fragment. This recombinant bacteriophage can be introduced into a host bacterium thereby "cloning" the foreign DNA into the host. The new genes are propagated and become a part of the genetic machinery of the bacterium host. The bacterium host thus acquires the genetic traits contributed by the new genes and is capable of "expressing" these traits.

In recombinant technology work, a formidable task has been encountered in being able to "screen" the transformed cells and select the cells which have acquired the desired genetic trait, i.e. the viable transformants (hosts). In certain bacteria strains, a means for "primary" selection exists, e.g., if the transformed bacteria is resistant to a certain antibiotic the bacteria can be cultured in the presence of such antibiotic and the cells which survive can be selected as viable transformants. This process, involving genes which are vital to the survival of the bacteria, is designated primary selection. In contrast, genetic traits which are not vital to the survival of the bacteria, e.g., production of extracellular enzymes such as $\alpha$-amylase, proteases, cellulases and hemicellulases cannot be selected on the basis of primary selection. There is thus a need for a recombinant technology method which is applicable to cloning both a gene for which primary selection does not exist, in addition to cloning a gene for which primary selection does exist.

The Bacillus genus contains approximately 48 species; virtually all of the species secrete a variety of soluble extracellular enzymes, under varying parental habitats. In addition, as discussed hereinafter, Bacillus microorganism also synthesize intracellular enzymes and antibiotics. Utilization of Bacillus microorganisms has reached commercial importance in such diverse fields as medicine and brewing. Further commercial utilization of Bacillus can be provided by the use of recombinant technology to allow the insertion of a variety of Bacillus genes encoding desired genetic traits into different Bacillus microorganisms such as *B. subtilis*.

It is known that genes encoding or regulating $\alpha$-amylase in a Bacillus strain can be introduced into *B. subtilis* if the two strains are sufficiently closely related, i.e., if there is extensive genetic homology between the two strains. This is referred to as homologous cloning. For example, *J. Bacteriol* 120: 1144–1150 (1974) describes the introduction of DNA from *B. subtilis var amylosaccharitus* having exceptionally high $\alpha$-amylase activity into a genetically similar (homologous) microorganism *B. subtilis Marburg* having relatively low $\alpha$-amylase activity. The transformed organisms produced acquired high $\alpha$-amylase activity.

However, most Bacillus are not sufficiently related to *B. subtilis*, i.e, are not sufficiently homologous, to permit the DNA obtained from one *Bacillus subtilis* strain to be efficiently introduced into a different Bacillus. *J. Bacteriol* 111: 705–716 (1972).

The literature (Kawamura, et. al.; *Gene* 5: 87–91 (1979)] describes a recombinant DNA technique which also involves insertion of DNA into a bacteriophage vector. Kawamura et. al. discloses isolation of chromosomal DNA fragments from a defective *B. subtilis* bacteriophage and insertion of the isolated DNA into another bacteriophage to produce a recombinant bacteriophage. The recombinant bacteriophage was then used in transformation of a *B. subtilis* microorganism and transformants were selected by conventional techniques. Because the chromosomal DNA was obtained from a defective *B. subtilis* bacteriophage, insertion of the DNA into a *B. subtilis* microorganism involved a homologous transformation. None of the prior art references discussed above discloses a method for introducing foreign DNA into a *B. subtilis* bacteriophage to produce a recombinant bacteriophage that can be used in heterologous cloning of genes.

SUMMARY OF THE INVENTION

The present invention is directed to a recombinant bacteriophage, a method for producing and selecting recombinant bacteriophage and a method for heterologous cloning of foreign DNA effective in biosynthesizing a desired genetic trait in a genetically heterologous Bacillus host microorganism.

The method for producing and selecting the recombinant bacteriophage involves obtaining genetic fragments encoding a desired genetic trait; isolating DNA fragments from a bacteriophage; ligating the genetic and DNA fragments to produce a mixture containing recombinant molecules; incubating the mixture with DNA from a second Bacillus which does not contain the desired genetic trait and which is substantially genetically homologous with the host Bacillus and is prototrophic for the growth requirement and incubated with a host Bacillus which is lysogenic for the bacteriophage and auxotrophic for a growth requirement to produce a mixture which contains transformed host Bacillus which are prototrophic for the growth requirement, lysogenic for the desired recombinant bacteriophage and which contain the desired genetic trait within the bacteriophage. Transformed host Bacillus are selected by growing the mixture on a growth medium which does not contain the growth requirement and determining the presence of the genetic trait. The recombinant bacteriophage containing the desired genetic trait is recovered from the host Bacillus by induction. *Bacillus subtilis* recombinant bacteriophage φ3T (ATCC 31595-B1) is claimed. The bacteriophage produced can be used in heterologous transformation by infecting a host Bacillus with the bacteriophage.

DESCRIPTION OF THE INVENTION

Chromosomal DNA encoding the desired extracellular enzyme is first obtained from Bacillus microorganisms, digested with an appropriate restriction enzyme, e.g., an enzyme isolated from *B. globigii* (Bgl 11) to cleave the DNA, and the enzyme inactivated. The DNA from a φ3T bacteriophage is similarly treated with a restriction enzyme and the enzyme inactivated. The DNA from the Bacillus microorganism and from the bacteriophage is then ligated by known techniques to produce a ligated mixture of DNA consisting of recombinant molecules. The recombinant molecule mixture contains randomly ligated mixtures of chromosomal DNA fragments, bacteriophage fragments and chromosomal fragments linked to bacteriophage fragments. [See *J. Bacteriol.* 121: 354–302 (1975)].

The mixture of recombinant DNA molecules is incubated with DNA isolated from a second Bacillus microorganism and with a host Bacillus microorganism. The sequence of incubation can be varied. The host Bacillus is lysogenic for the bacteriophage used and is also auxotrophic for a growth requirement. The second Bacillus microorganism does not contain the genetic fragment to be incorporated, is substantially genetically homologous with the host Bacillus and is prototrophic for the growth requirement. The concept of homologous and heterologous microorganisms is well-known and discussed in *J. Bacteriol.* 111: 705–716 (1972).

The step of incubating the host Bacillus with the homologous DNA which is prototrophic for the growth requirement is a technique for selecting Bacillus hosts which can react with DNA and therefor provide enrichment for transformed host microorganisms.

In order to determine which of the recombinant bacteriophages incorporated in the host Bacillus contain the desired genetic trait, the host Bacillus must be screened. In the present example, the host Bacillus are screened for the production of α-amylase by a conventional starch-iodine test. The recombinant bacteriophage can then be obtained from the host Bacillus by inducing the host.

The present embodiment described in the example utilizes homologous DNA prototrophic for threonine (Thr+) and a host Bacillus microorganism auxotrophic for threonine (Thr−). The identity of the auxotrophic growth requirement is not critical. Growth requirements for other amino acids or purines or pyrimidines could be used with the appropriate microorganism as well as such selective traits as antibiotic resistance. For example, suitable amino acids include lysine, tyrosine, alanine, leucine and serine. Suitable purines and pyrimidines include adenine, thymine, guanine, cytosine and thymine. Antibiotic resistant traits include resistance to erythromycin, spectinomycin and streptomycin.

The method of the present invention is suitable for cloning genes encoding such genetic traits as extracellular enzymes, intracellular enzymes and antibiotics. Extracellular enzymes include α-amylases, proteases, cellulases, hemicellulases, penicillinases and pectinases. Intracellular enzymes include lytic enzymes, glucose isomerase, polynucleotide phosphorylase, restriction endonuclease and dextranases. Antibiotics include edeine $A_1$ and $B_1$, bacitracin A, gramicidin A, tyrocidine and butirosin B.

The present example describes the use of φ3T bacteriophage. Other suitable bacteriophages include SP02 [See *Gene* 7: 51–58 (1971)] and Rholl (p11) [See *J. Virol.* 20: 509–519 (1976)].

Furthermore, the recombinant bacteriophage, containing genes encoding a desired trait can be introduced into host Bacillus microorganisms which already contains the genetic information for that desired trait, thus producing a host microorganism containing multiple genetic copies of that gene, i.e., multiple genes for the same trait. For example, a recombinant bacteriophage φ3T containing the α-amylase genes *B. amyloliquefaciensH* can be introduced into a *B. subtilis* which contains a functioning *B. subtilis* α-amylase gene to produce a *B. subtilis* which produces two α-amylases, one encoded by *B. amyloliquefaciensH* genes and one by *B. subtilis* genes.

As referred to earlier, recombinant technology directed to utilization of recombinant bacteriophages which involve incorporation of genes for which no primary selection exists presents major problems in screening for the desired transformants.

For example, if a transformation procedure is attempted for a gene for which a primary selection technique does not exist, each cell must be screened to detect possible transformants. The logistics are formidable; in a cloning experiment, a total of $10^8$ to $10^9$ cells may be grown. Approximately 100 cells can be conveniently cultured and grown for screening on a single petri dish. Thus it would require culturing and screening microorganisms on up to 10,000 petri plates to examine for all possible transformants. In contrast, the present method involves a cloning procedure which drastically reduces the screening task. Instead of the $10^8$ cells described above, the present method allows for a reduction to the order of magnitude of, e.g., $10^4$ to $10^5$ cells. These cells can then be cultured and grown for screening on 100 to 200 petri dishes, which reduces a nearly-impossible screening task to an easily managed task.

In the following Examples, various microorganisms are designated as having an ATCC number. Each microorganism so designated has been deposited with the American Type Culture Collection, Rockville, Md. and a culture of each is available to the public without restriction.

EXAMPLE 1

A. Preparation and Isolation of α-amylase Encoding Gene

Chromosomal DNA encoding α-amylase genetic information was obtained from *B. amyloliquefaciensH* RUB 500 (ATCC 31592) as described below. [See *J. Virol.* 14: 1013–1016 (1972)].

*B. amyloliquefaciensH* was grown in 50 to 100 ml of a peptone medium commercially available from Difco Laboratories, Detroit, Mich. under the trade designation Difco Penassay Broth. After about 18 hours of incubation with shaking at 37° C., the cells were harvested by centrifugation and washed twice and resuspended in 10 ml of a buffer which consisted of 0.15M tris(hydroxymethyl)aminomethane hydrochloride buffer, commercially available from Sigma Chemical, St. Louis, Mo. under the trade designation Trizma Base and 0.1M ethylenediamine tetraacetic acid (EDTA) at a pH of 8.0. The cell suspension was centrifuged again and lysed by suspending it in 5 ml of the above buffer solution, which additionally contained crystalline egg white lysozyme (1 mg per ml) for 30 minutes at 37° C. An enzyme to degrade protein, (1 mg/ml) was added and the culture was incubated at 50° C. for 10 minutes and then at 37° C. for 50 minutes. A suitable enzyme is available from Calbiochem, LaJolla, Calif. under the trade designation Pronase. The cytoplasmic membrane protein complex was removed from the DNA by treatment with a mixture of detergents made up of sodium lauryl sulfate and a detergent commercially available from Ciba-Geigy Corporation, Ardsley, N.Y., under the trade designation Sarkosyl NL-97. The detergent final concentration was about 2 percent weight/volume composed of equal parts of the above detergents.

Incubation was continued at 50° C. until total dissociation of the cytoplasmic membranes occurred. The DNA was then extracted three times using redistilled phenol saturated with a buffer made of 0.1M Trizma Base at a pH of 8.0. The DNA was precipitated by the addition of 0.1M NaCL with 10 ml cold 95 percent ethanol, wound on a glass rod, washed in three successive 70 percent ethanol solutions and redissolved in 10 mM Trizma Base containing 1 mM EDTA, at a pH of 7.5. The DNA was stored at 4° C. over chloroform.

The isolated DNA was then digested with the restriction enzyme *B. globigii* (Bgl 11) to hydrolyze the DNA. *B. globigii* is commercially available from Miles Laboratories, Inc., Elkhart, Ind. The Bgl 11 enzyme was then inactivated by heating the mixture to 68° C. for 15 minutes.

B. Preparation and Isolation of φ3T Bacteriophage

The bacteriophage used was φ3T, first isolated by Tucker as described in *J. Gen. Virol.* 4: 489–504 (1969). The φ3T used was obtained by growing bacteria strain RUB 830 (φ3T) as described below. RUB 830 φ3T has been described earlier [*J. Virol.* 21: 522–529 (1977)], and is available from the personal collection of Wilson and Young.

High titers of RUB 830 (φ3T) were obtained by growing RUB 830 in a growth medium (designed M) at 32° C. to a density of 50 Klett units (Klett-Summerson Colorimeter, filter no. 66) and inducing with mitomycin C (final concentration, 0.5 μg/ml). M medium contained: 10 gm of a pancreatic digest of casein commercially available from Difco Laboratories, Detroit, Mich. under the trade designation BactoTryptine; 5 gm yeast extract; 9.9 gm NaCl; and 1,000 ml distilled water. The mixture was autoclaved and a sterile solution of 5 ml of 1M $MgCl_2$ and 0.1M $MNCl_2$ added.

The RUB 830 (φ3T) bacteriophage was then digested with Bgl 11 restriction enzyme to hydrolyze the DNA. The Bgl 11 enzyme was then inactivated by heating the mixture to 60° C. for 15 minutes.

The DNA from *B. amyloliquefaciensH* and the φ3T were combined and ligated as described below. [See *J. Bacteriol.* 121: 354–362 (1975)].

C. Ligation Procedure

The ligase reaction was carried out in a final volume of 100μ liters. The DNA isolated from *B. amyloliquefaciensH* and the φ3T bacteriophage were mixed together, placed on ice and the following added: 50 mM $MgCl$ (10μ liters); 0.1M dithioerythritol (10μ liters); 0.5 mM adenosine triphosphate (10μ liters); water (20μ liters); and DNA ligase (1 U/mg DNA). The reaction mixture was incubated on ice for 12 hours at 14° C.

D. Incubation Procedure

The ligated mixture containing recombinant molecules was incubated with chromosomal DNA from a *B. subtilis* microorganism homologous to the host but prototrophic for a growth requirement for which the host Bacillus is auxotrophic to produce a bacteriophage vector.

100μ liter of the mixture containing the recombinant molecules from C. above was incubated with 100 μl (1 mg) of *B. subtilis* RUB 200 (ATCC 31593) DNA. RUB 200 is a strain that is prototrophic for threonine (Thr+) and defective in α-amylase biosynthesis (Amy−).

E. Transformation and Selection of Recombinant Bacteriophage

The entire mixture from above (200 μl) was incubated with 100μ liters of a host strain of *B. subtilis* RUB 201, (ATCC 31594). The host RUB 201 is auxotrophic for threonine (Thr−) and lysogenic for bacteriophage φ3T (as explained later). The incubation was carried out at 37° C. for 0.5 hour with aeration.

Samples (0.1 ml) of the incubated host were spread on plates of Spizizen's minimal agar (supplemented with 22 mM glucose, 20 μg/ml of each of the aromatic amino acids, tryptophane; phenylalanine; tyrosine and 1 percent soluble starch, but not containing threonine) in order to select for cells transformed to α-amylase biosynthesis (Amy+) and threonine independence (Thr+). Cells which were transformed from Thr− to Thr+, i.e., threonine independence have been transformed by incorporating DNA. Out of these cells, a certain number will have also taken up DNA fragments which include the α-amylase gene (Amy+).

Approximately $10^5$ cells were obtained which were viable in the absence of threonine. Cells which had not been transformed to Thr+ were not viable in the absence of threonine and did not survive. These transformants were then screened for α-amylase production by a conventional technique which involved flooding the petri dishes with $I_2$ solution. The presence of α-amylase-producing microorganisms was indicated by the appearance of a clear halo around such cells. The *B. subtilis* RUB 201 was transformed into *B. subtilis* RUB 204 (ATCC 31595) which contains the recombinant bacteriophage φ3T which has incorporated the genetic information for Amy+.

It was determined that out of the approximately $10^5$ cells transformed into Thr+, less than 10 cells were also transformed into α-amylase producing cells. The procedure described is reproducible. The example described was repeated and similar results were obtained. Approximately 7 Thr+ transformants capable of biosynthesizing α-amylase were obtained.

The φ3T carries a gene encoding thymidylate synthetase (thyP3) which can be used as a "marker". This marker can be used to demonstrate that the cloned α-amylase gene is "linked" to the φ3T gene and that the two are co-transformed. A series of experiments was carried out using donor DNA from *B. subtilis* RUB 204 encoding α-amylase (Amy+), bacteriophage φ3T and *B. subtilis* RUB 205 as the host bacterium. It was determined that each of the transformants which contained Amy+ contained bacteriophage φ3T which were Thy+, i.e., produced thymidylate synthetase. This is significant, because it demonstrates that the Amy+ and Thy+ are "linked", i.e., are on the same DNA fragment, and therefore insertion of the bacteriophage φ3T fragment into a host will increase the probability of "carrying" the desired Amy+ trait into the host. Expressed another way, the foreign DNA, e.g., Amy+ is "tacked" onto the φ3T bacteriophage and the φ3T bacteriophage "drags" the Amy+ into the host bacterium.

It was earlier indicated that the host *B. subtilis* RUB 201 was lysogenic for φ3T bacteriophage. In addition, the transformed host bacterium, containing the recombinant bacteriophage φ3T ATCC 31595-B1, i.e., the transformed host, is lysogenic for the recombinant bacteriophage φ3T. This means that the transformed host contains the recombinant bacteriophage φ3T in a dormant state (but encoding the Amy+ and the φ3T bacteriophage DNA). By the use of conventional techniques [*J. Virol.*, 24: 522–529 (1977)] the recombinant bacteriophage φ3T can be recovered from the transformed host by induction. Induction of the transformed host converts the dormant state recombinant bacteriophage φ3T into the vegetative cycle of reproduction. Therefore, the recombinant bacteriophage can be recovered and cultured to replicate itself. The recombinant bacteriophage can be further used to infect a new host Bacillus microorganism as described below.

EXAMPLE 2

Five *B. subtilis* RUB 204 transformants, containing the gene encoding α-amylase, produced as described in Example 1 were induced with mitomycin C and *B. subtilis* recombinant bacteriophage φ3T recovered.

Each of these five recombinant bacteriophages were used to infect a culture of *B. subtilis* RUB 200. The infection of RUB 200 was accomplished by incubating RUB 200 with the *B. subtilis* recombinant bacteriophage φ3T at a temperature of 37° C. for 30 minutes with aeration.

Samples of the incubated RUB 200 were plated in a peptone medium of tryptose blood agar plates and examined for infectious centers, i.e., plaques by conventional techniques [See *J. Virol.* 21: 522–529 (1977)].

Lysogens (bacterial cells contain the bacteriophage) were obtained from the plaque centers and subcultured on a medium containing starch and subsequently tested for the production of α-amylase by the starch-$I_2$ test described earlier. The lysogens formed produced a clear halo, indicating the presence of α-amylase production which indicated that the recombinant bacteriophage was successfully inserted into the bacteria host.

What is claimed is:

1. A method for producing and selecting *B. subtilis* recombinant bacteriophage φ3T (ATCC 31595-B1) containing the gene encoding biosynthesis of α-amylase suitable for use in heterologous transformation of a lysogenic host Bacillus microorganism which comprises the steps of:

(a) obtaining genetic fragments encoding α-amylase from *B. amyloliquefaciensH* RUB 500 (ATCC 31592);

(b) obtaining DNA fragements from a φ3T bacteriophage vector by treating said bacteriophage vector DNA with Bgl II restriction enzyme;

(c) ligating the genetic fragments obtained in step (a) with the DNA obtained in step (b) to produce a mixture containing a series of recombinant molecules suitable for transforming said lysogenic host Bacillus;

(d) incubating the mixture of step (c) with DNA isolated from a *B. subtilis* RUB 200 (ATCC 31593) microorganism which does not contain said genetic fragments obtained in step (a), said RUB 200 microorganism having substantial genetic homology with a host *B. subtilis* RUB 201 (ATCC 31594) and being prototrophic for threonine, to allow for selection of said lysogenic host Bacillus capable of reacting with DNA to provide suitable means for host Bacillus transformed with said desired genetic trait;

(e) incubating the mixture of step (d) with said host *B. subtilis* RUB 201 said host *B. subtilis* RUB 201 being lysogenic for said bacteriophage of step (b) and auxotrophic for threonine to produce a mixture containing host *B. subtilis* RUB 201 transformed into *B. subtilis* RUB 204 (ATCC 31595) which are prototrophic for threonine, lysogenic for said *B. subtilis* recombinant bacteriophage φ3T and which contain the gene encoding biosynthesis of α-amylase within said bacteriophage;

(f) selecting said transformed host *B. subtilis* RUB 204 by growing said mixture on a growth medium which does not contain threonine and determining the presence of α-amylase; and (g) obtaining therefrom *B. subtilis* recombinant bacteriophage φ3T (ATCC 31595-B1) containing the gene encoding biosynthesis of α-amylase by inducing said transformed host *B. subtilis* RUB 204.

2. Bacillus subtilis recombinant bacteriophage φ3T (ATCC 31595-B1) having incorporated therein the gene encoding biosynthesis of α-amylase suitable for use in heterologous transformation of Bacillus microorganisms.

* * * * *